United States Patent [19]

Blythin

[11] Patent Number: 5,350,755
[45] Date of Patent: Sep. 27, 1994

US005350755A

[54] COMPOUNDS AND METHODS FOR TREATING HYPERPROLIFERATIVE SKIN DISEASE

[75] Inventor: David J. Blythin, North Caldwell, N.J.

[73] Assignee: Schering Corporation, Kenilworth, N.J.

[21] Appl. No.: 917,925

[22] Filed: Jul. 21, 1992

Related U.S. Application Data

[63] Continuation of Ser. No. 686,314, Apr. 16, 1991, abandoned, which is a continuation of Ser. No. 504,704, Apr. 4, 1990, abandoned, which is a continuation of Ser. No. 207,904, Jun. 14, 1988, abandoned, which is a continuation of Ser. No. 938,217, Dec. 5, 1986, abandoned.

[51] Int. Cl.$^5$ .................................. A01N 43/42
[52] U.S. Cl. ........................... 514/278; 514/247; 514/248; 514/861; 514/863
[58] Field of Search ............... 514/247, 248, 278, 861, 514/863, 217

[56] References Cited

FOREIGN PATENT DOCUMENTS

| | | | |
|---|---|---|---|
| 0127135 | 12/1984 | European Pat. Off. | ............ 491/147 |
| 0144996 | 6/1985 | European Pat. Off. | ............... 471/10 |
| 07537 | 12/1986 | PCT Int'l Appl. | ......... A61K 31/44 |
| 00752 | 2/1987 | PCT Int'l Appl. | ........ A61K 31/435 |
| 2153348 | 8/1985 | United Kingdom . | |

OTHER PUBLICATIONS

*Current Therapy*, 1981 ed., ed. Conn, W. B. Saunders Company pp. 738, 739.
Merck Index, 8th ed. p. 862.
Merck Index, 9th ed. pp. 536, 629–630.

*Primary Examiner*—Joseph L. Schofer
*Assistant Examiner*—Peter D. Mulcahy
*Attorney, Agent, or Firm*—Henry C. Jeanette

[57] ABSTRACT

A method of treating hyperproliferative skin disease in a mammal with substituted spiro pyridine derivatives is disclosed. The compounds may be administered topically or by other conventional routes of administration.

9 Claims, No Drawings

COMPOUNDS AND METHODS FOR TREATING HYPERPROLIFERATIVE SKIN DISEASE

This is a continuation of application Ser. No. 07/686,314 filed Apr. 16, 1991, now abandoned, which is a continuation of application Ser. No. 07/504,704 filed Apr. 4, 1990, now abandoned, which is a continuation of application Ser. No. 07/207,904 filed Jun. 14, 1988, now abandoned, which is a continuation of application Ser. No. 06/938,217 filed on Dec. 4, 1986, now abandoned.

BACKGROUND OF THE INVENTION

The production of a spiro[cyclopentane]-quinolinedione is described in Chem. Pharm. Bull., 17, 1290 (1969). Several additional spiroquinoline diones are disclosed in Bull. Soc. Chim. Fr., 364 (1968). The references do not describe pharmaceutical uses for these compounds.

The compounds used in the method of this invention are disclosed in European published application No. 84 11 4974 published Jun. 19, 1985. No use for the treatment of hyperproliferative skin disease is disclosed therein.

SUMMARY OF THE INVENTION

This invention is a method of treating hyperproliferative skin disease in a mammal comprising administering an anti-hyperproliferative skin disease effective amount of a compound having the structural formula I:

wherein
W and X may be the same or different and are CH or N and are at any of the ring positions 5, 6, 7 or 8;
Y and Z may be the same or different and are O or S;
$R^1$ and $R^2$ may be the same or different and are hydrogen, alkyl having from 1 to 6 carbon atoms, halogen, nitro, alkoxy having from 1 to 6 carbon atoms or trifluoromethyl;
$R^3$ is independently hydrogen or alkyl having from 1 to 6 carbon atoms;
$R^4$ and $R^5$ may be the same or different and are hydrogen or are from 1 to 7 alkyl groups each of which having from 1 to 6 carbon atoms;
the spiro ring, M, may contain one optional double bond;
k is 0, 1 or 2;
l is an integer of from 3 to 6; and
A is phenyl, naphthyl, indenyl, indanyl, phenanthridinyl, pyridinyl, pyrimidinyl, pyrazinyl, pyridazinyl, 1,2,4-triazinyl, furyl, thiophenyl, benzofuranal, indolyl, imidazolyl, pyrazolyl, triazolyl, or thiazolyl any of which may be substituted with up to three of any of the following substituents, Q: hydroxy, alkyl having from 1 to 6 carbon atoms, halogen, nitro, alkoxy having from 1 to 6 carbon atoms, tri-fluoromethyl cyano, cycloalkyl having from 3 to 7 carbon atoms, alkenyloxy having from 3 to 6 carbon atoms, alkynyloxy having from 3 to 6 carbon atoms, $S(O)m-R^a$ {wherein m is 0, 1 or 2 and $R^a$ is alkyl having from 1 to 6 carbon atoms}, $NHSO_2R^a$ {wherein $R^a$ is defined herein}, $NHSO_2CF_3$, $NHCOCF_3$, $SO_2NH_2$, $COR^b$ {wherein $R^b$ is OH, $NH_2$ or $OR^a$ (wherein $R^a$ is defined herein)}, $O-B-COR^b$ {wherein B is alkylene having from 1 to 4 carbon atoms and $R^b$ is defined herein}, or $NHCOR^c$ {wherein $R^c$ is hydrogen, alkyl having from 1 to 6 carbon atoms, alkoxy having from 1 to 6 carbon atoms, $COR^d$ (wherein is hydroxy or alkoxy $R^d$ having from 1 to 6 carbon atoms) or $NHR^e$ (wherein $R^e$ is hydrogen or alkyl having from 1 to 6 carbon atoms)}.

A preferred method of treating hyperproliferative skin disease is the administration of a compound of formula I wherein Y and Z are both oxygen.

A second preferred method of treating hyperproliferative skin disease is the administration of a compound of structural formula II:

wherein $R^1$, $R^2$, $R^3$, $R^4$, $R^5$, M, A, k and l are defined herein.

A third preferred method of treating hyperproliferative skin disease is the administration of a compound of formula III:

wherein $R^4$, $R^5$, M, A and l are defined herein.

The invention also encompasses the administration of a pharmaceutical composition which comprises a compound of formula I in combination with a pharmaceutically acceptable carrier.

The compounds of formula I as defined above are disclosed in U.S. application Ser. No. 561,416 filed Dec. 14, 1983, now U.S. Pat. No. 4,652,564 the disclosure of which is incorporated herein by reference.

DESCRIPTION OF THE INVENTION

The compounds of the invention may be predated by reacting a properly substituted compound having the structural formula IV wherein A, W, X, Y, Z, $R^1$, $R^2$, $R^3$, $R^4$, $R^5$, k and l are as defined herein, and L is a substituent known to those skilled in the art as a "leaving group".

Treatment of compound IV with an organic base such as triethylamine or 1,8-diazabicyclo[5.4.0]undec-7-ene, DBU [Angew. Chem., Internat. Ed., 6 76 (1967)] in a nonreactive solvent such as methylene chloride will produce the compounds of the invention having structural formula I.

For purposes of predating a compound of formula I, II, III or IV a "leaving group" is defined as a substituent which may be displaced and carried a negative charge. Examples of such substituents are bromide, iodide, trifluoroacetoxy, p-toluene-sulfonyloxy, methanesulfonyloxy and the like. The preferred leaving group is bromide.

The compounds having structural formula IV wherein L is OH may be prepared by known methods from known starting materials.

Exemplary of such starting materials for preparing compounds having structural formula IV are 2anilio nicotinic acids which may be prepared, for example, as described in U.S. Pat. No. 26,655; and 2-phenylamino-3-pyrazine carboxylate esters which may be prepared substantially as exemplified herein starting with a 2-amino-3-pyrazine carboxylate ester. 2-Anilino-3-pyrazine carboxylic acid is a known compound, C.A. , 75, 20154e (1971 ) , which may -be esterified by standard procedures.

Compounds having structural formula IV wherein L is bromine may be prepared, for example, from the corresponding hydroxy compound by treatment with concentrated HBr (e.g. 48% HBr). Other desired leaving group substituents, L, may be prepared by known methods.

The compounds having structural formula wherein Y and/or Z are oxygen may be converted to the corresponding compound wherein Y and Z are sulfur by known methods. For example, treatment with Lawesson's Reagent [2,4-bis(4-methoxyphenyl)-1,3-dithia-2,4-diphosphetane-2,4-disulfide] in hot toluene will effect this conversion.

When utilized herein and in the appended claims the below listed terms, unless specified otherwise, are defined as follows:

halogen—fluorine, chlorine, bromine and iodine;

alkyl and alkoxy—comprised of straight and branched carbon chains containing from 1 to 6 carbon atoms;

alkenyloxy—comprised of straight and branched carbon chains containing from 3 to 8 carbon atoms and comprising a carbon to carbon double bond; and alkynyloxy—comprised of straight and branched carbon chains containing from 3 to 8 carbon atoms and comprising a carbon to carbon triple bond.

Certain compounds described herein may contain a double bond in the spiro ring, M. Those skilled in the art will recognize that such a double bond may not involve the "spiro" carbon atom, i.e., the 3-carbon atom identified in structural formula I.

The compounds described herein are comprised of a—$(CHR^3)_k$-substituent wherein the $R^3$ group may vary independently. Thus, for example, when k equals 2 the following patterns of substitution (wherein $CH_3$ is used to represent any substituent, $R^3$,) are contemplated: —$CH_2CH(CH_3)$—, —$CH(CH_3)CH_2$—, —$[C(CH_3)H$-$]_2$— and the like. In addition when k equals 2 substituents such as —$CH(CH_3)CH(C_2H_5)$—,—$CH(i$-$C_3H_7)CH(C_2H_5)$—are also contemplated.

Certain compounds of formula I through IV may contain up to 3 substituents, Q. When more than one such substituent, Q, is present they may be either the same or different.

Certain compounds of the invention may exist in isomeric forms. The invention contemplates all such isomers both in pure form and in admixture, including racemic mixtures.

The compounds described herein are useful for the treatment of hyperproliferative skin disease. used herein, the term "hyperproliferative skin disease" means any condition the symptoms of which include accelerated skin cell production, manifested as scaling, plaques or papular lesions. Examples of hyperproliferative skin diseases include Psoriasis, eczema, dandruff and the like. Effectiveness of the compounds for the treatment of hyperproliferative skin disease in mammals is demonstrated by the Arachidonic Acid Mouse Ear Test described below. The Arachidonic Acid Mouse Ear Test is a recognized model for assessing the effectiveness of compounds for the treatment of hyperproliferative skin disease.

ARACHIDONIC ACID MOUSE EAR TEST, MATERIALS AND METHODS

Charles River, female, CD, (SD) BR mice, 6 weeks old, are caged 8/group and allowed to acclimate 1–3 weeks prior to use.

Arachidonic acid (AA) is dissolved in reagent Grade acetone (2 mg/0.01 ml) and stored at −20° C. for a maximum of 1 week prior to use. Inflammatory reactions are induced by applying 10 ul of AA to both surfaces of one ear (4 mg total ) .

Test drugs are dissolved in either reagent grade acetone or aqueous ethanol (only if insoluble in acetone) at the same doses selected by Opas et al., Fed. Proc. 43, Abstract 2983, D. 1927 (1984) and Young et al., J. Invest. Dermatol. 82, Dr). 367-371 (1984 ) . These doses are employed to ensure maximum responses and to overcome any difference in topical absorption which could occur with any drug applied in an aqueous ethanol vehicle. The test drug is applied 30 minutes prior to challenge with AA.

The severity of the inflammation is measured as a function of increased ear weight. A 6 mm Dunch biopsy is removed 1 hour after AA challenge and weighed to the nearest 0.1 mg. Mean±standard error and all possible comparisons are made via Duncan's Multiple Range Statistic.

A representative example of the compounds of formula I and effectiveness of such compounds for the treatment of hyperproliferative skin disease is demonstrated below in Table I.

TABLE I

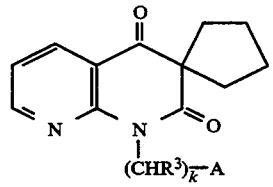

$X = N, W = CH, Y = O, Z = O,$
$[CR^4R^5]_1 = -(CH_2)_4-$, $R^1$ and $R^2 = H$

| —$(C^HR^3)_k$—A | Dose (mg/ear) | Tissue Wt. (g) | % Inhibition |
| --- | --- | --- | --- |

TABLE I-continued

| Structure | | | |
|---|---|---|---|
| 4-Cl-phenyl | 1.0 | 1.33 ± 0.40 | 82% |
| 3-Cl-phenyl | 0.1 | 2.01 ± 0.69 | 72% |

As a result of the administration of a compound of formula I, a remission of the symptoms of hyperproliferative skin disease can be expected. Thus, for example, one affected by psoriasis can expect a decrease in scaling, erythemia, size of plaques, pruritus and other symptoms associated with psoriasis. The dosage of medicament and the length of time required for successfully treating each individual psoriatic patient may vary, but those skilled in the art of medicine will be able to recognize these variations and adjust the course of therapy accordingly.

When administered for the treatment of hyperproliferative skin disease, the compounds may be administered topically, orally, rectally or parenterally. When administered topically, the amount of compound administered varies widely with the amount of skin being treated, as well as with the concentration of active ingredient applied to the affected area. When administered orally, the compounds of formula I are effective for the treatment of hyperproliferative skin disease at doses ranging from about 0.1 mg to about 100 mg, which may be administered in divided doses. When administered rectally, the compounds-of formula I maybe administered in doses ranging from about 0.1 mg to about 1000 mg. When administered parenterally, the compounds of formula I are effective for the treatment of hyperproliferative skin disease in doses ranging from about 0.1 mg/kg body weight to about 10 mg/kg body weight which may be administered in divided doses.

Included within the invention are preparations for topical application to the skin whereby the compounds having structural formula I are effective in the treatment and control of skin diseases characterized by rapid rates of cell proliferation and/or abnormal cell proliferation, e.g. psoriasis.

In a preferred method of carrying out the invention, a pharmaceutical formulation comprising a compound of formula I together with a non-toxic, pharmaceutically acceptable topical carrier, usually in concentrations in the range of from about 0.001 percent to about 10 percent, preferably from about 0.1 percent to about 5 percent, is applied several times daily to the affected skin until the condition has improved. Topical applications may then be continued at less frequent invervals (e.g. once a day) to control mitosis in order to prevent return of severe disease conditions.

The compounds of formula I can exist in unsolvated as well as solvated forms, including hydrated forms. In general, the solvated forms, with pharmaceutically acceptable solvents such as water, ethanol and the like are equivalent to the unsolvated forms for purposes of the invention.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary; binding properties in suitable proportions and correlated in the shade and size desired. The powders and tablets are comprised of from 5 or 10 to about 70 percent active ingredient on a weight/weight basis. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

The compounds of formula I may be conveniently applied in a liquid solvent, such as a water-miscible liquid carrier made up of hydrophilic liquids having a high solvating action, e.g., a solution which comprises, for example, propylene glycol and polyethylene glycol. Alternatively, the compounds may be applied in dry form, such as a powder. Other forms in which the compounds may be used topically include creams, lotions, aerosols, dusts and ointments which are prepared by combining a compound as defined in formula I with conventional pharmaceutical diluents and carriers commonly used in topical dry, liquid, cream and aerosol formulations.

The ointments and creams may, for example, be formulated with an aqueous oily base with the addition of suitable thickening and/or gelling agents. Such bases may thus, for example, include water and/or oil such as liquid paraffin or vegatable oil, such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulated with an aqueous or oily base and will, in general, also include one or more of the following, namely, stabilizing agents, emulsifying agents, dispensing agents, suspending agents, thickening agents, coloring agents, perfumes and the like.

Powders may be formed with the aid of any suitable powder base, e.g., talc, lactose, starch, etc.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component to water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to 100 mg according to the particular application and the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following formulations exemplify some of the dosage forms in which the compounds of the invention may be employed. In each, the active ingredient is the compound 1'-(3-chlorophenyl) spiro [cyclopentane-1, 3'(1,8)naphthyridine]-2',4'-(1'H)-dione, and is referred to as "active compound". However, any other compound of formula I may be substituted into the examples described herein.

FORMULATIONS
Formulation I: Ointment

| Formula | mg/g |
|---|---|
| Active Compound | 1.0–20.0 |
| Benzyl Alcohol, NF | 10.0 |
| Mineral Oil, USP | 50.0 |
| White Petrolatum, USP to make | 1.0 g |

PROCEDURE

Mix and heat to 65° C., a weighted quantity of white petrolatum, mineral oil, benzyl alcohol, and cool to 50°–55° C. with stirring. Disperse active compound in a portion of the mineral oil and then add to the above mixture with stirring. Cool to room temperature.

Formulation II: Cream

| Formula | mg/g |
|---|---|
| Active Compound | 1.0–20.0 |
| Stearic Acid, USP | 60.0 |
| Glyceryl Monostearate | 100.0 |
| Propylene Glycol, USP | 50.0 |
| Polyethylene Sorbitan Monopalmitate | 50.0 |
| Sorbitol Solution, USP | 30.0 |
| Benzyl Alcohol, NF | 10.0 |
| Purified Water, USP to make | 1.0 g |

PROCEDURE

Heat the stearic acid, glyceryl monostearate and polyethylene sorbitan monopalmitate to 70° C. In a separate vessel, dissolve sorbital solution, benzyl alcohol, water, and half quantity of propylene glycol and heat to 70° C. Add the aqueous phase to oil phase with high speed lightning stirring. Dissolve the active compound in remaining quantity of propylene glycol and add to the above emulsion when the temperature of emulsion is 37°–40° C. Mix uniformly with stirring and cool to room temperature.

Formulation III: Gel

| Formula | mg./g |
|---|---|
| Active Compound | 1.0–20.0 |
| Propylene Glycol, USP | 300.0 |
| Butylated Hydroxytoluene | 5.0 |
| Carbomer 940 | 5.0 |
| Sodium Hydroxide (added as a 1% w/w solution in proplyene glycol) | 0.7 |
| Polyethylene Glycol 400, USP | 669.3–688. |

PROCEDURE

Prepare a 1% solution of the sodium hydroxide in propylene glycol and hold. Add approximately one-half the remaining propylene glycol, and the polyethylene glycol 400 to a suitable vessel and mix. Dissolve the butylated hydroxytoluene in this mixture. Disperse the carbomer 940 in the above mixture with vigorous agitation. Add the solution of sodium hydroxide with high speed agitation to bring pH up to 7 and recirculation until a thick gel forms. Dissolve the active compound in the remaining propylene glycol and add to the gel slowly as the gel is continuously recirculated.

| Formulation IV: Lotion | |
| --- | --- |
| Formula | mg/g |
| Active Compound | 1.0–20.0 |
| Carbomer 940 | 3.0 |
| Sodium hydroxide (charged as 4% w/w aqueous solution) | 0.05 |
| Isopropyl Alcohol | 40.00 |
| Purified Water, USP to make | 1.0 g |

PROCEDURE

Prepare a 4% solution of sodium hydroxide in water. Heat the purified water to 60° C. Add carbomer 940 and mix at high speed until dispersed. Cool the above mixture to room temperature and slowly charge sodium hydroxide until uniform. Add 80% of isopropyl alcohol to the above with mixing. Dissolve the active compound in remaining isopropanol. Add this to the mixture with stirring. Adjust pH to 5.0 to 5.5 with sodium hydroxide, if necessary.

| Formulation V: Topical Aerosol | |
| --- | --- |
| Formula | mg/g |
| Active Compound | 1.0–20.0 |
| Caprylic/Capric Triglyceride | 50.00 |
| Mineral Oil | 20.00 |
| Specially Denatured Alcohol | 150.00 |
| Hydrocarbon Aerosol Propellant q.s. ad. | 1.0 g |

PROCEDURE

Add and mix the caprylic/capric triglyceride mineral oil and specially denatured alcohol in a suitable compounding tank. Add the active compound drug and continue mixing until the active compound is dissolved or dispersed uniformily. Fill the concentrate into cans and then fill the required amount of hydrocarbon aerosol propellant.

The quantity of active compound in a unit dose of preparation may be varied or adjusted from 1 mg to 100 mg according to the particular application and the potency of the active ingredient. The compositions can, if desired, also contain other therapeutic agents.

The amount of active compound applied to the involved lesions may be varied depending upon the requirements of the patient, the severity of the condition being treated and the particular compound being employed. Determination of the proper dosage for a particular situation is within the skill of the art. For convenience, the total daily dosage may be divided and administered in portions during the day if desired.

PREPARATIVE EXAMPLE 1

4-Hydroxy-3-(4-hydroxybutyl)-1-phenyl-1,8-naphthyridin-2(1H)-one

A mixture of methyl 2-phenylamino-nicotinate (100g.), ε-caprolactone (1000g.) and potassium t-butoxide (200g.) was stirred at room temperature, in a nitrogen atmosphere, for 1/2 hr. It was heated at 45° C. for 1 hr. then at 85° C. for 2 hrs. and finally at 105° C. for 3 hr.

The hot mixture was poured carefully into 8L of 5% KOH solution and was stirred overnight.

The mixture was extracted with 2L of ether and the aqueous phase was retained. It was extracted again with a fresh 2L of ether. The clear aqueous phase was adjusted to pH 4.5 with conc. HCl to yield a white solid which was filtered off, washed with water and dried to yield 4-hydroxy-3-(4-hydroxybutyl)-1-phenyl-1,8-naphthyridin-2(1H)-one, m.p. 205.5°–206.5° C. (from isopropanol).

By substituting the relevant ester and lactone in this preparative example intermediates to many other compounds of the invention may be prepared.

PREPARATIVE EXAMPLE 2

4-Hydroxy-3-(3-hydroxypropyl)-1-phenyl-1,8-naphthyridin-2(1H)one

Methyl 2-phenylamino-nicotinate (25g.) was dissolved in δ-valerolactone (240g.) with stirring in an atmosphere of nitrogen. To the resulting solution was added potassium t-butoxide (50g.) and the mixture was stirred at room temperature for 1/2 hr. It was then heated to 100° C. for 3 hr. after which time it was poured into 1L of 5% NaOH solution and stirred overnight.

The mixture was extracted (2X) with IL of ether then the aqueous layer was adjusted to pH 4.5 with conc. HCl. The solid which separated was filtered off, washed with water and dried to yield 4-hydroxy-3-(3-hydroxypropyl)-1-phenyl-1,8-naphthyridin-2(1H)-one, m.p. 218°–220° C.

By utilizing the correspondingly substituted starting materials in the procedures of preparative examples 1 or 2, the following compounds were obtained:

1-(4-chlorophenyl)-4-hydroxy-3-(3-hydroxypropyl)-1,8-naphthyridin-2(1H)one, m.D. 249.5°–251° C.;
4-hydroxy-3-(3-hydroxypropyl)-1-(4-methylphenyl)-1,8-naphthyridin-2(1H)one, m.p. 227°–228° C.;
4-hydroxy-3-(3-hydroxypropyl)-1-(4-methoxyphenyl)-1,8-naphthyridin-2(1H)one, m.D-229°–231° C.;
1-(3,4-dichlorophenyl)-4-hydroxy-3-(3-hydroxypropyl)-1,8-naphthyridin-2(1H)one, m.p. 230°–232° C.;
1-(4-chlorophenyl ) -4-hydroxy-3-(4-hydroxybutyl ) -1,8-naphthyridin-2(1H)one, m.p. 238°–240° C.;
4-hydroxy-3-(4-hydroxybutyl ) -1-(4-methylphenyl ) -1,8 -naphthyridin-2(1H)one, m.p. 186°–188° C.;
4-hydroxy-3-(4-hydroxybutyl ) -1-(4-methoxyphenyl ) -1,8-naphthyridin-2 (1H)one, m.p. 237°–239° C.;
1-(3,4-d i chlorophenyl ) -4-hydroxy-3-(4-hydroxybutyl ) -1,8-naphthyridin-2 (1H)one, m.p. 188°–190° C.;
1-(3-chlorophenyl ) -4-hydroxy-3-(4-hydroxybutyl ) -1,8-naphthyridin-2-(1H)one, m.p. 176°–178° C.;
4-hydroxy-3-(4-hydroxybutyl)-1-(3-methoxyphenyl)-[1,8]-naphthyridin-2 (1H)-one, m.p. 217°–219° C.;
4-hydroxy-3-(4-hydroxybutyl ) -1-phenyl-quinoli n-2 (1H) -one, m.p. 156.5°–158° C.

PREPARATIVE EXAMPLE 3

Ethyl 5-(4-hydroxy-2-oxo-1-phenyl-1H-[1, 8] naphthyridin-3-yl) pentanoate

Methyl 2-phenylaminonicotinate (8.5g.) was dissolved with stirring in diethyl pimelate (80 ml. ) an atmosphere of nitrogen. To the mixture was added potassium t-butoxide (13g.) and the mixture was stirred at room temperature for 1 hr. It was then heated to 135°–140° C. for 6 hours after which time it was poured into water. The aqueous layer was extracted with methylene chloride and then adjusted to pH 4.5 with conc. HCl. Solid sodium chloride was added after which the solid was filtered off, washed with water and dried, m.p. 168°–169° C.

By substituting diethyl suberate for diethylpimelate in the above procedure; ethyl 6-(4-hydroxy-2-oxo-1-phenyl-1H-[1,8] naphthyridin-3-m.p. 167°–168° C. was obtained.

PREPARATIVE EXAMPLE 4

4-Hydroxy-3-(5-hydroxypentyl) -1-phenyl-1,8-naphthyridin-2(1H) one

To a suspension of ethyl 5-(4-hydroxy-2-oxo-1-phenyl-1H-[1,8]-naphthyridin-3-yl)pentanoate (1g.) (prepared as in preparative example 3) in dry dioxane (50 ml.) in an atmosphere of nitrogen is added lithium borohydride (0.34 g.). The mixture is stirred at room temperature for 20 min. then it is heated to 60° C. for 16 hrs.

The product is poured into water, adjusted to pH 4.5 with acetic acid and the resulting solid is filtered off. The solid is washed with water and dried to yield 4-hydroxy-3-(5-hydroxypentyl) -1-phenyl-1,8naphthyridin-2-(1H) -one.

PREPARATIVE EXAMPLE 5

3-(4-Bromobutyl)-4-hydroxy-1-phenyl, 1,8-naphthyridin-2(1H) one

In 47% HBr (100 ml.) was dissolved 4-hydroxy-3(4-hydroxybutyl) -1-phenyl-1,8-naphthyridin-2 (1H) -one (5g) in an atmosphere of nitrogen at room temperature. After 1 hr. the solution was heated to 90° C. and it was kept there for 6 hrs.

After cooling, the product was poured into 1L of H2O and the pH was adjusted to 5 with potassium acetate. After stirring for 5 minutes, the solid was filtered off, washed with water and dried to yield 3-(4bromobutyl) -4-hydroxy-1-phenyl-1, 8-naphthyridin-2 (1H) one, m.p. 194°–196° C.

By substituting the appropriate starting materials and using the procedure as above, the following additional compounds were obtained:

3-(4-bromobutyl)   -4-hydroxy-1-(3,4-dichlorophenyl)-1,8-naphthyridin-2 (1H) one, m.

3-(4-bromobutyl) -4-hydroxy-1-(4-chlorophenyl )-1,8-naphthyridin-2 (1H)one, m.p. 228

3-(4-bromobutyl ) -1-(3-hydroxyphenyl)-4-hydroxy-1,8-naphthyridin-2(1H)one, m.p. 214°–216° C.;

3-(4-bromobutyl)-1-(3-methoxyphenyl)-4-hydroxy-1,8-naphthyridin-2 (1H)one, m.p. 179.5°–181° C.;

3-(4-bromobutyl)-1-(3-chlorophenyl)   -4-hydroxy-1,8-naphthyridin-2(1H)one, m.p. 195.5°–197° C.; and 3-(4-bromobutyl )-4-hydroxy-1-phenyl-quinolin-2(1H) one, m.p. 206.5°–208° C.

PREPARATIVE EXAMPLE 6

Methyl-2-phenylamino-3-pyrazine carboxylate (A) Methyl 2-bromo-3-pyrazine carboxylate To a stirred mixture of 12.7g. of methyl 2amino pyrazine carboxylate and 47 ml. of 48% hydrobromic acid there was added, dropwise, 12.6 ml. of bromine keeping the temperature at 0°. A solution of 14.4g. of sodium nitrite in 60 ml. of water was then added, dropwise, at 0° and the reaction mixture stirred for 15 minutes. The reaction mixture was basified to pH 8 with sodium bicarbonate and extracted with ethyl acetate and again with chloroform. The organic layers were dried over magnesium sulfate, filtered and concentrated to a yellow oil. Recrystallization from ether-hexane yielded the product, m.p. 43°–45° C.

(B) Methyl 2-phenylamino-3-pyrazine carboxylate

A mixture of 9.5g. of methyl 2-bromo-3pyrazine carboxylate, 8.2g. of aniline, 0.5g. of ptoluene sulfonic acid and 100 ml. of water was stirred and refluxed for two hours. The reaction mixture was poured on ice, extracted with ethyl acetate, the organic extracts were dried and concentrated to yield an oil. The crude residue was eluted on a silica gel column with ethyl acetate-hexane (1:2) yielding the product of this example as a yellow solid, m.p. 72°–75° C.

PREPARATIVE EXAMPLE 7

3-(2-Hydroxyethyl) -4-hydroxy-1-phenyl-1,8-naphthyridin-2 (1H) one

To a solution of 6.8g. of methyl 2-phenyl-amino-3-pyridine carboxylate in 60 ml. of gamma-butyrolactone there was added, under nitrogen, 13.4g. of potassium tertiary butoxide. The reaction mixture was heated and stirred for one hour at 95° C., poured on ice and stirred overnight. The mixture was extracted with ether, the aqueous layer acidified with acetic acid to pH 4.5 and the product was collected by filtration. Recrystallization from chloroform, acetone, isopropanol yielded the product of this example as a colorless solid; m.p. 235°–236° C.

PREPARATIVE EXAMPLE 8

3,9-Dihydro-9-phenyl-furo[2,3-b][1,8]-naphthyridin-4(2H) -one

A solution of 4-hydroxy-3-(2-hydroxyethyl)-1-phenyl-1,8-naphthyridin-2 (1H) -one in Eaton's Reage P2O5 in methane sulfonic acid; 40 ml.) was stirred in an atmosphere of nitrogen and was heated to 70° C. for 2 hr. After cooling, the product was poured into water, adjusted to pH 4 with NaHCO3, filtered, washed with water, air dried and recrystallized from isopropanol with decolorization to yield the product, m.p. 245°–247° C.

EXAMPLE 1

1′-Phenylspiro[cyclopentane-1,3′-(1,8)-naphthyridine]-2′, 4′-(1′H)dione

A suspension of 3-(4-bromobutyl)-4-hydroxy-1-Phenyl-1,8-naphthyridin-2(1H)one (5g.) in methylene chloride (350 ml.), in an atmosphere of nitrogen, was stirred at room temperature and to it was added triethylamine (4.1 ml.). The mixture was stirred at room temperature for 16 hrs. Water (300 ml.) was added and the aqueous layer was adjusted to pH 4.5 with hydrochloric acid. The organic layer was separated and the aqueous layer was back-extracted with methylene chloride. The combined organic layers were washed with water, dried (Na2SO4), filtered and evaporated to yield a solid which was recrystallized from-isopropanol to yield 1′-phenylspiro[cyclopentane-1,3′-(1,8) naphthyridine]2′,4′-(1′H)dione, m.p. 178°–179° C.

By utilizing the appropriately substituted starting materials in the above-described procedure, the following products were obtained:

1′-(4-methylphenyl) spiro[cyclopentane-1,3′-(1,8) naphthyridine]-2′, 4′-(1′H)-dione, m.p. 177°–179.5° C.;

1′-(4-chlorophenyl ) spiro[cyclopentane-1,3′-(1,8) naphthyridine]-2′,4′-(1′H)-dione, m.p. 181.5°–183° C.;

1'-(3,4-dichlorophenyl) spiro[cyclopentane-1,3'-(1,8) naphthyridine]-2', 4'-(1'H)-dione, m.p. 143°–145.5° C.;

1'-(3-chlorophenyl) spiro[cyclopentane-1,3'-(1,8) naphthyridine]-2', 4'-(1'H)-dione, m.p. 165°–167° C.;

1'-(3-methoxyphenyl) spiro[cyclopentane-1,3'-(1,8) naphthyridine]-2', 4'-(1'H)-dione, m.p. 159°–160.5° C.;

1'-(3-hydroxyphenyl)spiro[cyclopentane-1,3'-(1,8)naphthyridine]-2', 4'-(1H)-dione, m.p. 218°–220° C.;

1'-phenylspiro[cyclopentane-1,3'-quinoline]-2', 4'-(1H)dione, m.p. 166°–168

In general, by following the procedures described in Preparative Examples 1, 4, 5 or 6, or an art-recognized modification thereof, using lactones with desired substituents, other intermediates, II (B=O), may be prepared which are useful for preparing products of the invention by the method of Example 1.

EXAMPLE 2

1'-Phenylspiro[cyclohex-3-ene]-1,3'-[1,8]-naphthyridine]-2', 4'-(1H)dione, m.p. 218°–220° C.;

A.

4-Hydroxy-3-(5-hydroxy-3-pentynyl)-1-phenyl-1,8-naphthyridin-2(1H)-one.

A solution of 3,9-dihydro-9-phenyl-furo [2,3-b][1,8] naphthyridin-4[2H]-one (prepared as in Example 8) in dimethylsulfoxide/tetrahydrofuran(DMSO/THF) is stirred and cooled to ca. 0° C. while to it is added a pre-formed solution of the sodium salt of the tetrahydropyranyl (THP) ether of propargyl alcohol Na+ $^-$C≡C—CH$_2$—O-THP) which is prepared from the THP ether of propargyl alcohol and an equivalent amount of dimsyl sodium in DMSO/THF. Dimsyl sodium is prepared by refluxing the desired amount of sodium hydride in DMSO/THF (1:10) until reaction is complete.

The reaction is allowed to warm up until reaction is observed, (monitor by t.l.c.). When complete the reaction is made sufficiently acidic to remove the protecting group, and the product is isolated.

B.

(Z)-4-Hydroxy-3-(5-hydroxy-3-pentenyl)-1-phenyl-1,8-naphthyridin-2 (1H) one

The acetylene (from part A) is dissolved in methanol containing 2% by weight (of the acetylene) of 5% palladium on barium sulfate which also contains pure quinoline in amount equal to the weight of the catalyst. The mixture is hydrogenated at atmospheric pressure until one equivalent of hydrogen is taken up. Filtration and evaporation produces the product.

C. 1'-Phenyl spiro[(cyclohex-3-ene)-1,3'-[1,8]-naphthyridine]-2', 4'-(1H) -dione.

The cis-olefin (from part B) is dissolved/suspended in pyridine at 0° C. A slight excess of mesyl chloride (1.05 equivalents) is added and the mixture is stirred until reaction is complete (monitor by t.l.c.). The pyridine is removed under high vacuum and the residue is dissolved in CH$_2$Cl$_2$. The solution is washed with a small volume of cold water, dried, and treated with an excess (1.2 equivalents) of triethylamine. When reaction is complete the crude product is isolated by washing the CH$_2$Cl$_2$ with water, evaporation and chromatography in CH$_3$CN:H$_2$O (80:20) over reversed-phase silica (Whatman Partisil (40; ODS-3), yields the product.

I claim:

1. A method of treating psoriasis or eczema in a mammal, comprising administering in combination with a pharmaceutically acceptable carrier a compound having the structural formula:

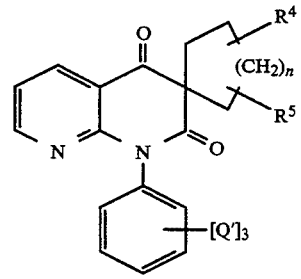

wherein n is 1, 2 or 3; $R^4$ and $R^5$ are hydrogen, methyl or ethyl and Q' is hydrogen, hydroxy, alkyl having from 1 to 6 carbon atoms, halogen, nitro, alkoxy having from 1 to 6 carbon atoms, trifluoromethyl, cyano, cycloalkyl, having from 3 to 7 carbon atoms, alkenyloxy having from 3 to 6 carbon atoms, alkynyloxy having from 3 to 6 carbon atoms, $S(O)_m$-$R^a$ {wherein m is 0, 1 or 2 and $R^a$ is alkyl having from 1 to 6 carbon atoms}, NHSO$_2$R$^a$ {wherein $R^a$ is defined herein}, NHSO$_2$CF$_3$, SO$_2$NH$_2$, COR$^b$ {wherein $R^b$ is OH, NH$_2$ or OR$^a$(wherein R$^a$is defined herein)}, O-B-COR$^b$ {wherein b is alkanediyl having from 1 to 4 carbon atoms and R$^b$ is defined herein}, or NHCOR$^c$ {wherein R$^c$ is hydrogen, alkyl having from 1 to 6 carbon atoms, alkoxy having from 1 to 6 carbon atoms, COR$^d$(wherein R$^d$ is hydroxy or alkoxy having from 1 to 6 carbons atoms) or NHR$^e$ (wherein R$^e$ is hydrogen or alkyl having from 1 to 6 carbon atoms)}.

2. The method defined in claim 1 wherein the compound is:

1'-phenylspiro[cyclopentane-1,3'-(1,8)naphthyridine]-2', 4'-(1'H)-dione;

1'-(4-methylphenyl)spiro[cyclopentane-1,3'-(1,8)-naphthyridine]-2', 4'-(1'H)-dione;

1'-(4-chlorophenyl)spiro[cyclopentane-1,3'-(1,8)-naphthyridine]-2', 4'-(1'H)-dione;

1'-(3,4-dichlorophenyl)spiro[cyclopentane-1,3'-(1,8)-naphthyridine]-2', 4'-(1'H)-dione;

1'-(3-chlorophenyl)spiro[cyclopentane-1,3'-(1,8)-naphthyridine]-2', 4'-(1'H)-dione;

1'-(3-methoxyphenyl)spiro[cyclopentane-1,3'-(1,8)-naphthyridine]-2', 4'-(1'H)-dione; or 1'-(4-hydroxyphenyl)spiro[cyclopentane-1,3'-(1,8)-naphthyridine]-2', 4'-(1'H)-dione.

3. The method of claim 2 wherein the compound administered is 1'-(3-chlorophenyl) spiro[cyclopentane-1,3'(1,8)naphthyridine]-2',4'-(1'H)-dione.

4. The method as defined in claim 2 wherein the compound of formula I is administered topically.

5. The method as defined in claim 1 wherein the compound is administered as a pharmaceutical composition comprising the compound of formula I in combination with a pharmaceutically acceptable carrier.

6. The method as defined in claim 5 wherein the pharmaceutical composition is an ointment.

7. The method as defined in claim 5 wherein the pharmaceutical composition is a cream.

8. The method as defined in claim 5 wherein the pharmaceutical composition is a lotion.

9. The method as defined in claim 5 wherein the pharmaceutical composition is an aerosol.

* * * * *